US00PP13149P2

(12) United States Plant Patent
Collicutt et al.

(10) Patent No.: US PP13,149 P2
(45) Date of Patent: Oct. 29, 2002

(54) MONARDA PLANT NAMED 'PETITE WONDER'

(75) Inventors: Lynn M. Collicutt, Lowe Farm (CA); Campbell G. Davidson, Morden (CA)

(73) Assignee: Her Majesty the Queen in right of Canada, as represented by the Minister of Agriculture, Ottawa (CA)

( * ) Notice: Subject to any disclaimer, the term of this patent is extended or adjusted under 35 U.S.C. 154(b) by 22 days.

(21) Appl. No.: 09/828,886

(22) Filed: Apr. 10, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Burns, Doane, Swecker & Mathis, LLP

(57) ABSTRACT

A new and distinct variety of perennial Monarda spp. or Bee-Balm plant is provided that exhibits a dense dwarf stature. The blossoms exhibit an attractive light pink coloration (as illustrated). Dense dark green and glossy foliage is formed that contrasts well with the blossom coloration. The new variety can be distinguished from the 'Petite Delight' variety (U.S. Plant Pat. No. 10,784) by its generally smaller blossom size, smaller foliage, and slightly smaller and more compact growth habit. The winter hardiness is good.

2 Drawing Sheets

BOTANICAL/COMMERCIAL CLASSIFICATION

Figure 1:
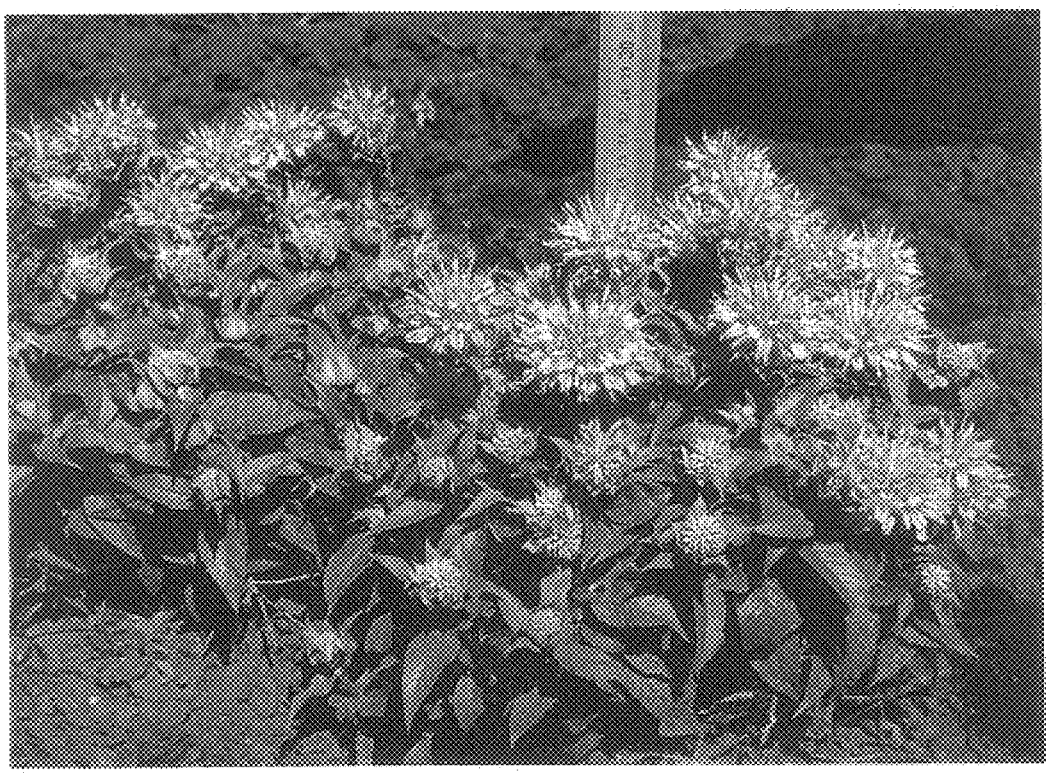

*Monarda didyma*×*Monarda fistulosa menthaefolia*/ Monarda Plant.

VARIETAL DENOMINATION cv. 'Petite Wonder'.

SUMMARY OF THE INVENTION

The new and distinctive perennial Monarda spp. (Bee Balm) variety of the present invention was the result of a breeding program involving open pollinated and controlled crosses that was carried out at the Morden Research Centre, Morden, Manitoba, Canada. The initial female parent (i.e., the seed parent) was *Monarda didyma* 'Cambridge Scarlet' (non-patented in the United States) and the initial male parent (i.e., the pollen parent) was *Monarda fistulosa menthaefolia* (non-patented in the United States). The initial cross created the 'Souris' variety (non-patented in the United States). Plants designated 60-1, 62-0, 64-8, 66-1, 76-1 and 75-1 were created in subsequent generations through the open pollination of the 'Souris' variety and offspring that were derived from the 'Souris' variety. Plants 76-1 and 75-1 next were crossed to create a plant designated 78-1. The open pollination of plant 78-1 resulted in the creation of the 'Marshalls Delight' variety (non-patented in the United States). See, *HortScience,* 24(3):525 (1989) where the 'Marshalls Delight' variety is discussed. Next, the 'Marshalls Delight' variety was open pollinated to form a plant designated 86-2. Plant 86-2 subsequently was open pollinated to form offspring from which the new variety of the present invention was selected during 1997. The single plant of the new variety found among the offspring.

The same series of open pollination and controlled crosses yielded the 'Petite Delight' variety (U.S. Plant Pat. No. 10,784).

It was found that the new Monarda spp. variety of the present invention:

(a) Forms attractive light pink blossoms that tend to be smaller in size than the 'Petite Delight' variety,
(b) Exhibits attractive dense dark green and glossy foliage that is generally smaller than that of the 'Petite Delight' variety,
(c) Exhibits a dwarf growth habit that is slightly smaller and more compact than the 'Petite Delight' variety, and
(d) Exhibits good winter hardiness.

The 'Marshalls Delight' variety lacks the low-growing dwarf growth habit of the new variety of the present invention. Also, the new variety of the present invention can be readily distinguished from the 'Petite Delight' variety by its generally smaller blossom size, smaller foliage, and slightly smaller and more compact growth habit.

The new variety well meets the needs of the horticultural industry and can be grown as attractive ornamentation in parks, gardens, public areas, and residential landscapes.

Beginning in 1997 at Morden, Manitoba, Canada, the new variety of the present invention has been asexually reproduced by the use of rhizome and softwood stem cuttings, division, and tissue culture. The characteristics of the new variety have been found to be strictly transmissible by such asexual propagation from one generation to another.

The new variety has been named 'Petite Wonder'.

BRIEF DESCRIPTION OF THE PHOTOGRAPHS

The accompanying photographs show, as nearly true as it is reasonably possible to make the same in color illustrations of this character, typical specimens of the plant and plant parts of the new variety. The Monarda plants described herein were photographed while growing at Morden, Manitoba, Canada.

FIG. 1—illustrates flowering plants of the new variety while growing in the landscape. The compact dwarf stature, dense dark green glossy foliage, and light pink blossoms in various stages of opening are shown.

Figure 2:
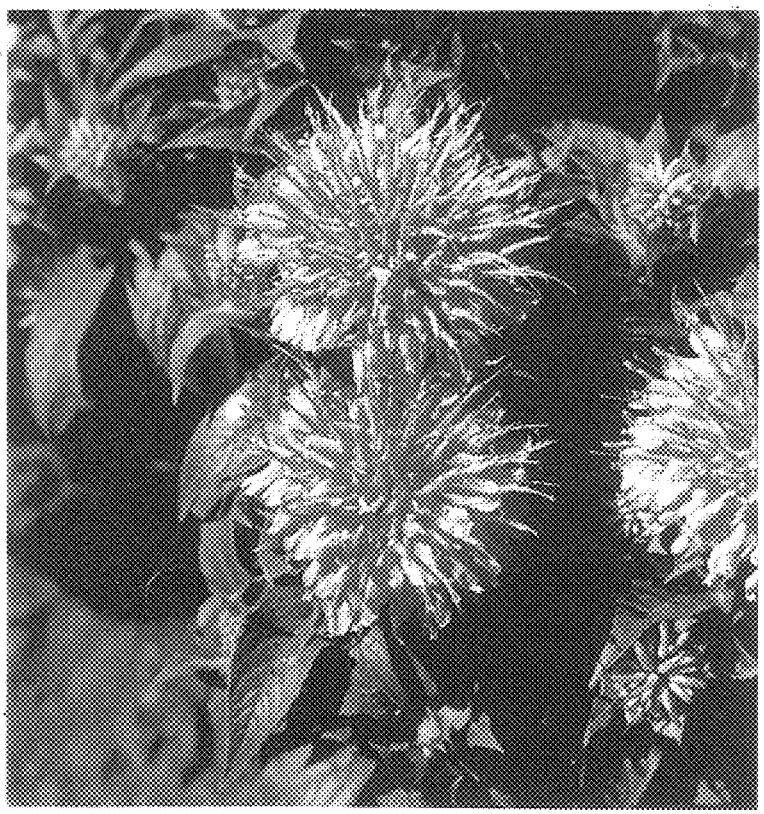

FIG. 2—illustrates a closer view of typical specimens of the blossoms and foliage of the new variety.

Figure 3:
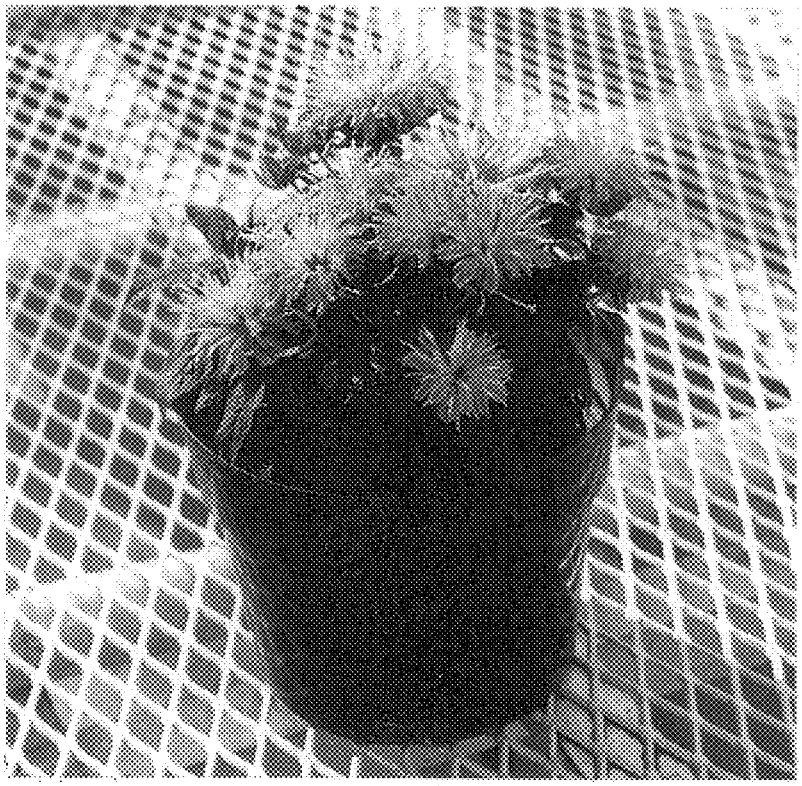

FIG. 3—illustrates a typical young container grown plant of the new variety.

Figure 4:
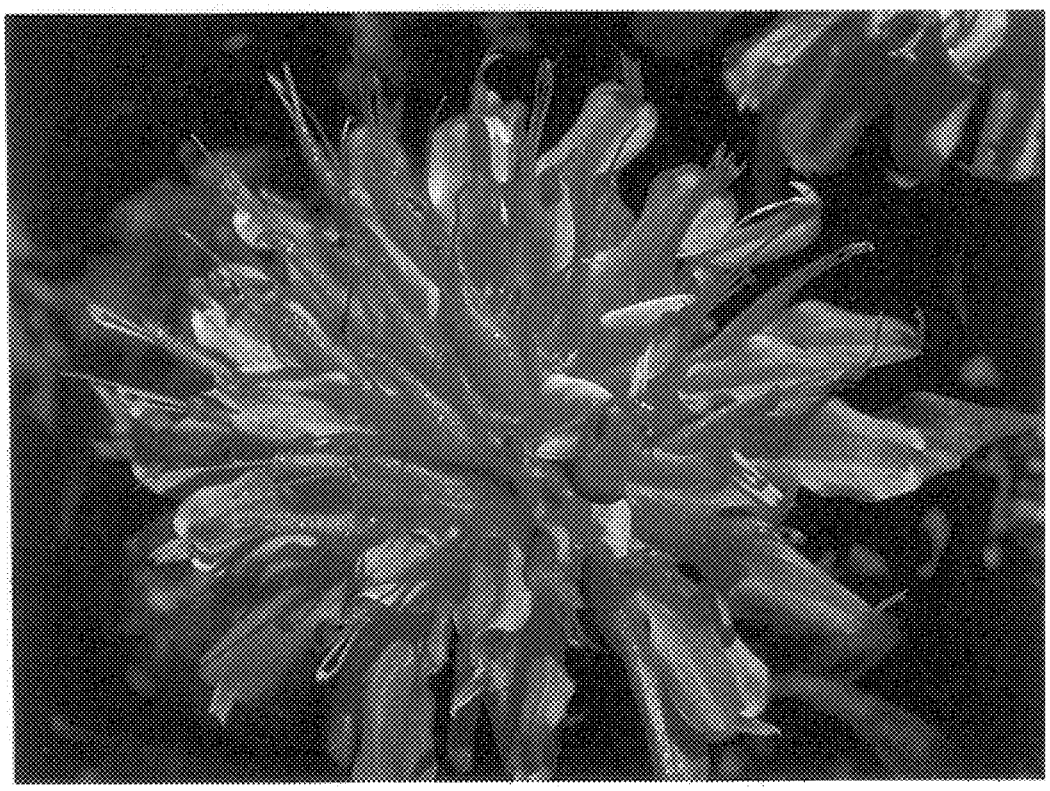

FIG. 4—illustrates a very close view of a typical specimen of a blossom of the new variety.

DETAILED DESCRIPTION

The chart used in the identification of the colors is that of The Royal Horticultural Society (R.H.S. Colour Chart). Common color terms are to be accorded their ordinary dictionary significance. The description is based on the observation of plants of the new variety while being grown outdoors in the landscape during the summer at Morden, Manitoba, Canada. The plants had an age of approximately three years from the planting of rooted cuttings.

Botanical classification: *Monarda didyma*×*Monarda fistulosa menthaefolia,* cv. 'Petite Wonder'.

Plant:

*Growth habit.*—Dwarf, compact, and round to oval in configuration.

*Size.*—Commonly approximately 23 to 25 cm in height and width. Slightly smaller and more compact than the 'Petite Delight' variety (U.S. Plant Pat. No. 10,784). This can be compared to a height and width of approximately 50 to 60 cm. for the 'Marshalls Delight' variety.

Foliage:

*Size.*—Leaves commonly measure approximately 56 mm in length on average and approximately 21 mm in width on average. The leaves tend to be slightly smaller than those of the 'Petite Delight' cultivar. Also, the leaves commonly tend to be somewhat smaller with shorter internode lengths due to the indicated dwarf growth habit than those of the 'Marshalls Delight' variety.

*Margins.*—Serrate.

*General appearance.*—Dense, dark green and glossy. The foliage typically is more glossy than that of the 'Marshalls Delight' variety. When viewed from a distance the appearance is similar to that of a bedding Chrysanthemum plant.

*Color.*—Dark green, near Yellow-Green Group 137B (upper surface), and near Yellow-Green Group 147B (under surface). As would be expected, there is some variation in leaf color with environmental conditions and the time of assessment within the growing season.

*Stems.*—Four-sided.

Inflorescence:

*Borne.*—Terminally, and dense compound (verticillaster).

*Number of flowers per inflorescence.*—Varies with environmental conditions and commonly ranges from approximately 25 to 50.

*Size.*—Approximately 50 mm in diameter on average. This can be compared to a diameter of approximately 60 to 65 mm for the 'Petite Delight' variety.

*Color.*—Light pink, Red-Purple Group 73A. The coloration varies somewhat depending upon the age of the blossoms and the season of the year. For instance, the intensity of the coloration tends to diminish and to become lighter with blossom age. The light pink coloration of the blossoms tends to be lighter than that of the 'Petite Delight' variety. This can be compared to a typical blossom coloration of Red-Purple Group 63B for the 'Marshalls Delight' variety.

*Corolla.*—Tubular and becomes progressively more open acropetally. Nectaries are located in the throat and usually on the upper side of the corolla tube that produce nectar. The bottom portion (i.e., the tongue) of the tubular flower is rounded with a slight notch in the middle that gives the appearance of three lobes. The top portion is very tubular in configuration and generally surrounds the reproductive components. The tubular flower is approximately 1 to 2 mm in diameter at the point of attachment. The texture of the petals is smooth and velvety. The lower lip of the tongue is slightly wavy.

*Calyx.*—Five-lobed and tubular and the coloration commonly is green with some reddish tinges.

*Stigma.*—Commonly protrudes beyond the edges of the petals, is generally white in coloration, and two-cleft at the apex.

*Style.*—Long and slender and generally white in coloration.

*Ovary.*—Deeply four-parted.

*Stamen.*—Attached to the throat near the opening, but generally below where the upper and lower portions of the corolla lips meet. The anther-bearing stamens are exerted.

*Anthers.*—Narrowly oblong (linear) and two-celled, and approximately 2 mm in size.

*Filaments.*—Slender and generally white in coloration. Two groupings commonly are visible that vary in height by approximately 2 to 4 mm.

*Pollen.*—Present and spheroidal in configuration.

*Flower duration.*—Approximately 6 to 8 weeks beginning during mid-August at Morden, Manitoba, Canada.

*Fragrance.*—The flowers, stems and foliage are aromatic and typical of *Monarda didyma* and *Manarda fistulosa.*

*Fruit and seeds.*—The fruit comprises four generally ovoid nutlets (seeds) and generally remains attached to the stock until the seeds are disseminated. The seeds may remain in the calyx over the winter and commonly fall out when the calyx deteriorates during the next season. The seeds are small, generally smooth, brown to dark brown in coloration, round or round-oval and are typical of the species. The length commonly is approximately 2 to 3 mm and the width commonly is approximately 1 to 2 mm.

Development:

*Vegetation.*—Good vigor.

*Culture.*—Plants should be cut back in the spring to remove older foliage and to promote new growth. Care should always be exercised so as not to damage the crown of the plant. The plants preferably are dead-headed after flowering to improve the visual appearance. The regrowth of the foliage after flowering is good thereby serving to maintain a fresh green appearance late in the growing season and throughout the fall.

*Disease resistance.*—During the course of observations to date powdery mildew has not posed a major problem. Some occurrence of powdery mildew has been observed during test plantings in the midwestern United States. Some rust (*Puccinia menthae*

*Pers.*) has been observed, but such rust involvement generally has taken place late in the season and was not severe. In comparative trials the new variety was rated "very good" for disease resistance when compared to other commonly-grown Monarda varieties.

*Insect resistance*.—Due to the high levels of essential oils in the flowers and foliage of Monarda spp. insects are commonly not a problem. In fact, Monarda leaves have been used in the past as a repellent to various insects. See, D. K. Weaver et al., *J. of Chemical Ecology* 21:127–142 (1995), and U.S. Pat. No. 5,306,497 to F. W. Dunkel et al.

*Hardiness*.—Plants are hardy to at least Agriculture Canada Zone 3 with no winter protection other than naturally occurring snowfall. See Quellette and Sherk, Woody Ornamental Plant Zonation III, Suitability Map for Probable Winter Survival of Ornamental Trees and Shrubs, *Can. J. Plant Sci.,* 47:3513–3518 (1967). Due to the low-growing habit of the new variety, natural snow cover is believed likely to be capable of extending the growing range to even colder regions.

*Propagation*.—Plants of the new variety can be readily propagated by the use of rhizome and softwood stem cuttings, division, and tissue culture. The use of rhizome cuttings has proven to be a very successful technique to rapidly increase the variety. For instance, approximately 30 rhizome cuttings can be obtained from a two to three year-old plant. Rhizome segments of approximately 2.5 to 5 cm in length with 0.5 to 1 cm of terminal growth can be harvested in early spring or fall and inserted into a potting medium and grown in a greenhouse or outdoors under protection. It is not recommended to use rhizome cuttings having significant vegetative leaf growth. Softwood stem cuttings should be taken early in the growing season and rooted under intermittent mist. Rooting success drops dramatically in the mid-summer. Cuttings will root without the use of a rooting hormone; however, the use of such hormone will speed the rooting process. Division has been successful for small increases with a two year-old plant being capable of yielding approximately six divisions. Tissue culture protocols can be utilized.

*Usage*.—The new variety can be used in traditional formal beds to provide attractive mid- to late-season blooms. Large mass plantings are possible. Floral designs can be easily sculpted while using the new variety in combination with other low-growing herbaceous plants. Plants can be used as specimens or as borders defining sections of beds or defining boundaries. The shiny, dark green foliage contrasts well with the light pink flowers.

We claim:

1. A new and distinct variety of Monarda spp. plant having the following combination of characteristics:

(a) Forms attractive light pink blossoms that tend to be smaller in size than the 'Petite Delight' variety, (b) Exhibits attractive dense dark green and glossy foliage that is generally smaller than that of the 'Petite Delight' variety, (c) Exhibits a dwarf growth habit that generally is slightly smaller and more compact than the 'Petite Delight' variety, and (d) Exhibits good winter hardiness;

substantially as herein shown and described.

* * * * *